US009546407B2

(12) United States Patent
Wald

(10) Patent No.: US 9,546,407 B2
(45) Date of Patent: Jan. 17, 2017

(54) MIXTURE TO INCREASE THE EFFECTIVENESS OF ANTISEPTICS AND/OR DISINFECTANTS, AN AGENT CONTAINING THE MIXTURE, AND THE USE OF THIS MIXTURE

(71) Applicant: WALD PHARMACEUTICALS S.R.O., Prague (CZ)

(72) Inventor: Tomas Wald, Prague (CZ)

(73) Assignee: WALD PHARMACEUTICALS S.R.O., Prague (CZ)

( * ) Notice: Subject to any disclaimer, the term of this patent is extended or adjusted under 35 U.S.C. 154(b) by 0 days.

(21) Appl. No.: 14/870,019

(22) Filed: Sep. 30, 2015

(65) Prior Publication Data

US 2016/0095320 A1    Apr. 7, 2016

(30) Foreign Application Priority Data

Oct. 1, 2014    (CZ) .................... 2014-676

(51) Int. Cl.
| | |
|---|---|
| A01N 63/00 | (2006.01) |
| A01N 47/44 | (2006.01) |
| A61K 31/155 | (2006.01) |
| A61K 8/43 | (2006.01) |
| A61K 8/66 | (2006.01) |
| A61K 45/06 | (2006.01) |
| A61K 38/48 | (2006.01) |
| A61Q 17/00 | (2006.01) |
| A61Q 11/00 | (2006.01) |
| A61K 38/54 | (2006.01) |
| A61K 9/00 | (2006.01) |
| A01N 63/02 | (2006.01) |
| A61K 9/08 | (2006.01) |
| A61K 36/232 | (2006.01) |
| A61K 36/28 | (2006.01) |
| A61K 36/45 | (2006.01) |
| A61K 36/534 | (2006.01) |
| A61K 36/537 | (2006.01) |
| A61K 36/61 | (2006.01) |
| A61K 36/73 | (2006.01) |

(52) U.S. Cl.
CPC ....... *C12Y 304/22002* (2013.01); *A01N 47/44* (2013.01); *A01N 63/02* (2013.01); *A61K 8/43* (2013.01); *A61K 8/66* (2013.01); *A61K 9/00* (2013.01); *A61K 9/0056* (2013.01); *A61K 9/08* (2013.01); *A61K 31/155* (2013.01); *A61K 36/232* (2013.01); *A61K 36/28* (2013.01); *A61K 36/45* (2013.01); *A61K 36/534* (2013.01); *A61K 36/537* (2013.01); *A61K 36/61* (2013.01); *A61K 36/73* (2013.01); *A61K 38/54* (2013.01); *A61Q 11/00* (2013.01); *A61Q 17/005* (2013.01); *C12Y 304/21001* (2013.01); *C12Y 304/21004* (2013.01); *C12Y 304/22032* (2013.01); *A61K 2800/5922* (2013.01); *A61K 2800/92* (2013.01)

(58) Field of Classification Search
USPC .................................. 424/49, 422
See application file for complete search history.

(56) References Cited

U.S. PATENT DOCUMENTS

| | | | | | |
|---|---|---|---|---|---|
| 4,693,888 | A | * | 9/1987 | Miyahara | ............... A23G 3/368 106/35 |
| 5,002,769 | A | * | 3/1991 | Friedman | ............. A61K 9/0063 424/422 |
| 2003/0211053 | A1 | | 11/2003 | Szeles et al. | |
| 2003/0211054 | A1 | | 11/2003 | Szeles et al. | |
| 2004/0018157 | A1 | | 1/2004 | Masters et al. | |
| 2004/0105874 | A1 | | 6/2004 | Bott et al. | |
| 2006/0177383 | A1 | | 8/2006 | Gebreselassie et al. | |
| 2008/0064711 | A1 | * | 3/2008 | Friedman | ............. A61K 9/0031 514/277 |

FOREIGN PATENT DOCUMENTS

| | | |
|---|---|---|
| WO | WO-90/10434 | 9/1990 |
| WO | WO 03/003976 | 1/2003 |
| WO | WO 2010/057140 | 5/2010 |
| WO | WO 2010/114549 | 10/2010 |
| WO | WO 2013/072932 | 5/2013 |

OTHER PUBLICATIONS

Czech Search Report for corresponding Czech Application No. PV 2014-676 mailed on Apr. 10, 2015.
Mudr. Michal Pokorny "Pouziti Chlorhexidinu v Gynekologii" New EU Magazine of Medicine Jan. 2, 2013 pp. 17-21.
Setu Mathur et al. "Chlorhexidine: The Gold Standard in Chemical Plaque Control" National Journal of Physiology, Pharmacy & Pharmacology | 2011 | vol. 1 | Issue 2 | 45-50.
Sala Othman et al. "The Effect of Chlorhexidine Supplementation in a Periodontal Dressing" Acta Odontologia Scandinavica, 47:6, pp. 361-366. 1989.
Christopher G. Jones "Chlorhexidine: is it still the gold standard?" Periodontology2000, vol. 15, pp. 55-62 1997.
Linda McCoy et al. "Adverse events associated with Chlorhexidine use" JADA, vol. 139 Feb. 2008.
William J Killoy "The Use of Locally-Delivered Chlorhexidine in the Treatment of Periodontitis." Journal of Clinical Periodontal 1998; 25: 953-958.

* cited by examiner

*Primary Examiner* — Walter Webb
(74) *Attorney, Agent, or Firm* — Pearl Cohen Zedek Latzer Baratz LLP

(57) ABSTRACT

The invention relates to the increase (improvement) of the effectiveness of antiseptics and/or disinfectants administered in a mixture with hydrolytic or proteolytic enzymes to a mucous membrane, a skin of a mammal or inanimate surfaces in the form of a solution, gel, paste, capsules or other as an agent. The use of the mixture is also stated.

17 Claims, 4 Drawing Sheets

MIXTURE TO INCREASE THE EFFECTIVENESS OF ANTISEPTICS AND/OR DISINFECTANTS, AN AGENT CONTAINING THE MIXTURE, AND THE USE OF THIS MIXTURE

CROSS REFERENCE TO RELATED APPLICATIONS

This application claims priority of Czech Patent Application No. PV 2014-676, filed Oct. 1, 2014, which is hereby incorporated by reference.

FIELD OF THE INVENTION

The invention relates to the increase (improvement) of the effectiveness of antiseptics and/or disinfectants administered in a mixture with hydrolytic or proteolytic enzymes to a mucous membrane, a skin of a mammal or inanimate surfaces in the form of a solution, gel, cream, emulsion, paste, capsules or other as an agent.

BACKGROUND OF THE INVENTION

Antiseptics are substances intended for application to a living tissue of a mammal, which is an animal or human, to a mucous membrane in order to suppress the risk of infection, sepsis, or putrefaction.

Disinfectants are substances intended for application to non-living materials in order to destroy micro-organisms. Given the nature of the definition of antiseptics and disinfectants, some substances may simultaneously perform both antiseptic and disinfectant roles, according to their use. Depending on the concentration of the used substance with antiseptic or disinfectant activity, the given substances may have bacteriostatic or bactericidal effect. Substances with antiseptic or disinfectant activity may be prepared via chemical synthesis or isolated from plants, animals or their products (for example propolis or herbal products).

Antiseptics and disinfectants act using a non-specific mechanism against a wide spectrum of bacteria G+ and G−, fungi, viruses and yeasts.

Typical disinfectants and antiseptics include substances derived from quaternary ammonium salt (e.g., cetylpyridinium chloride), chlorhexidine and its salts (e.g., digluconate), phenolic compounds, sodium bicarbonate, terpenes, hypochlorite (calcium, sodium), peroxides, boric acid, and acetic acid. Widely used antiseptics include Povidone iodine, Benzalkonium, Aminotridecan, Benzydamine, Dichlorobenzyl alcohol/Amylmetacresol, hexetidine, and other substances with a proven disinfectant or antiseptic activity.

Natural antiseptics and disinfectants include for example extracts of *Agrimonia eupatoria*, Peppermint, *Matricaria chamomilla*, cloves, fennel, *Salvia officinalis*, *Potentilla erecta*; and other substances with a proven disinfectant or antiseptic activity.

One of the most typical antiseptics and disinfectants is chlorhexidine, a substance included in the WHO Model List of Essential Medicines, it has long been used for its excellent antibacterial activity. This may be, depending on the concentration, either bacteriostatic or bactericidal.

In gynaecology, chlorhexidine is used, due to its high effectiveness, to treat vaginal discharges and mixed infections (bacterial vaginosis and vulvovaginal candidiasis), (Pokorny M., New EU Magazine of Medicien 1-2/2013). In obstetrics, it is used for the treatment of umbilical cord of newborn babies. In veterinary medicine, chlorhexidine is used as a disinfectant of the skin, wounds and instruments.

In dentistry, it is used primarily for its ability to inhibit plaque formation and to suppress inflammation of the gums (gingivitis, parodontosis) in the oral cavity. Moreover, chlorhexidine is in dentistry used as the "gold standard" in testing of other substances, which are expected to inhibit plaque formation or suppress inflammation of the gums (gingivitis, parodontosis) (Jones C. G., Chlorhexidine: is it still a gold standard? Perio2000; 1997:15:55-62). Chlorhexidine acts on the bacterial wall in a non-specific manner, when it even at low concentrations disrupts the osmotic balance of the cell wall and the cytoplasmic membrane through the formation of non-selective pores. Cytoplasmic fluids then escape through these pores and this leads to necrosis.

The chlorhexidine molecule consists of two symmetrical 4-chlorophenyl rings and two bisguanide groups connected by a central hexamethylene bridge. It is a strongly basic molecule. At pH higher than 3.5, it has two positive charges carried on both sides of the hexamethylene bridge (Albert A., Surgeant E. R.; In: ionization constants of acids and bases. London; 1962:Methuen, P.173).

Primarily, according to the art, chlorhexidine is used in the form of salt (hydrochloride, acetate or digluconate).

Chlorhexidine has a broad-spectrum of activity against micro-organisms. This includes gram negative and gram positive bacteria, viruses (including HIV and HBV), yeasts, fungi, dermatophytes. Chlorhexidine is used in the form of gels, mucoadhesive gels, mouthwashes, sprays, chewing gums, toothpastes and other. Furthermore, it is used in dressings intended for postoperative conditions in the oral cavity (Othman S., Hauge E., Germo P.; The effect of chlorhexidine supplementation in periodontal dressing. Acta Odont Scand 1989:47:361). In addition, chlorhexidine is used in locally administered agents with controlled release of the active substance at the site of affliction (e.g. Periochip) (Killoy W. J., The use of locally delivered Chlorhexidine in the treatment of periodentitis. Clinical results. J Clin Periodontol, 1998:25:953-958).

Clinical indications of chlorhexidine are stated by, for example (Natl J Physiol Pharm Pharmacol. 2011; 1(2): 45-50; Chlorhexidine: The gold standard in chemical plaque control, http://www.scopemed.org/?mno=8252).

Chlorhexidine is widely used as an antiseptic for treatment of mucous membranes or soft tissues, both in humans and animals. For short-term use, for example in oral cavity, chlorhexidine is used as:

1) A supplement to a mechanical plaque removal when brushing teeth and during professional prophylaxis to maintain good oral hygiene;
2) After oral surgery, including periodontal surgery or the root treatment;
3) As an immediate prophylactic agent for the prevention of postextraction bacteremia;
4) An agent for recurrent mouth ulcers;
5) An agent for treatment of stomatitis caused by dentures and for treatment of dry sockets;
6) An agent during the treatment of oral infections and acute necrotizing ulcerative gingivitis It is known that chlorhexidine can significantly reduce oral bacteria and prevent oral infection.

Chlorhexidine is used in intermittent short or medium term for:
1) Oral hygiene of physically and mentally disabled;
2) Physically compromised patients predisposed to oral infection;

3) Patients with high risk of dental caries;
4) Patients with extensive prosthetic reconstruction of abutment teeth with reduced periodontal support;
5) Patients with a dental implant.

However, the main limitation of a long-term administration of chlorhexidine, for example in preventive dentistry, is its side effect of teeth surface discolouration, back of the tongue, temporary deterioration in taste perception, reversible swelling of the parotid gland, burning and the formation of painful lesions.

However, a long-term administration of chlorhexidine is commonly used:
1) In patients with reduced tolerance to bacterial infection because of serious health problems, or as a result of a medicamentous treatment, which would include patients who have, for example agranulocytosis, leukaemia, haemophilia, thrombocytopenia, renal disease, allergy, underwent bone marrow transplantation, AIDS and another;
2) In patients who are treated with cytotoxic drugs, radiotherapy or immunosuppressants;
3) In patients with intermaxillary anchorage;
4) In patients who are mentally unwell;
5) In patients with physical disabilities or impaired motor functions;
6) In geriatric patients.

The main local adverse effect of chlorhexidine in dentistry is exogenous discolouration of teeth. As early as after a few days of use of chlorhexidine, dark yellow or brown spots appear on own or false teeth. Intensity of staining is mainly related to the used concentration of the chlorhexidine and the differences in the structure of the enamel in individual patients. Other side effects include c, buds for the perception of salty taste are affected most significantly (ref 25 of the same). Sometimes burning and the formation of painful lesions of the oral mucosa are reported which appears to be an idiosyncratic reaction and is dependent on the concentration used (ref 26 of the same). Supragingival calculus may form increasingly more. Chlorhexidine on its own has a bitter taste, which is very difficult to disguise. Irritation of the oral cavity with local allergy symptoms may also occur. During the placebo-controlled clinical trials in adult patients, the following adverse effects were reported with a frequency of less than 1%: Mouth ulcers, gingivitis, trauma, ulcerations, erythema, desquamation, a coated tongue and keratinisation.

Side effects of the use of chlorhexidine digluconate in relation to mucous membranes are mentioned by, for instance (J Am Dent Assoc. 2008 February; 139(2):178-83. Adverse events associated with chlorhexidine use: results from the Department of Veterans Affairs Dental Diabetes Study. McCoy L C, Wehler C J, Rich S E, Garcia R I, Miller D R, Jones J A.)

The following side effects are associated with chlorhexidine gluconate mucous membrane:
Common side effects of chlorhexidine gluconate mucous membrane:
Tooth discoloration;
Increase of tartar formation on the teeth;
Discoloration of the mouth;
Taste problems;
Rare but serious side effects of chlorhexidine gluconate mucous membrane:
Inflammation of the salivary glands;
Inflammation of skin caused by an allergy;
Life threatening allergic reaction;
Reaction due to an allergy;
Rare side effects of chlorhexidine gluconate mucous membrane:
Reduced sensation in the mouth;
Abnormal redness of the lining of the mouth;
Inflammation of the salivary gland;
Dry mouth;
Canker sore;
Mouth irritation;
Painful, red or swollen tongue;
Sore tongue.

From the art according to published international application WO 90/10434 (filed Mar. 15, 1990) it is known, that some of these chlorhexidine deficiencies can be addressed by adding physiologically acceptable copper salt. Among other things, however, the copper compounds are physiologically acceptable to the organism with relative difficulty.

Therefore, it is clear that there is a need to partially or entirely suppress the aforementioned existing disadvantages of antiseptics, such as chlorhexidine.

The aim of the invention is that at lower concentrations, of for example chlorhexidine, in the mixture, the above negative effects are suppressed or substantially eliminated, while its antiseptic and/or disinfectant properties are maintained.

BRIEF SUMMARY OF THE INVENTION

The inventor has surprisingly found that during the administration of antiseptic and/or disinfectant, advantageously chlorhexidine in mixture with at least one hydrolytic or proteolytic enzyme, it is possible to reduce the concentration of chlorhexidine approximately 3-5 times the concentration of the standard used (0.03% by weight-2% by weight) while achieving the same effect in the inhibition of bacterial growth.

It was found that the use of proteolytic/hydrolytic enzymes in appropriate concentrations in a mixture with chlorhexidine in the form of salt, especially when applied to the oral cavity, on mucous membranes or to the skin or inanimate materials in the appropriate form, thus had a synergistic inhibitory effect on the tested bacterial strains.

The essence of the invention is a mixture to increase the efficiency of antiseptics and/or disinfectants in hygiene of the oral mucosa and/or a skin of a mammal or inanimate surfaces, with the inhibition of bacterial growth. The mixture is characterised in that it contains chlorhexidine digluconate as the antiseptic and/or disinfectant with antimicrobial, antivirotic or antimycotic activity and at least one proteolytic or hydrolytic enzyme, and the total content of chlorhexidine digluconate is 0.001% by weight to 1% by weight, and the total content of at least one proteolytic or hydrolytic enzyme is 0.01% by weight to 2% by weight, based on the total weight of the mixture, the remainder up to 100% by weight is buffered saline, and water.

A mammal means, in accordance with the invention, a human or an animal.

In an advantageous embodiment to the invention, the inhibitor content in the mixture is from 0.001 to 1% by weight of the antiseptic and/or the disinfectant and 0.01 to 2% by weight of at least one proteolytic or hydrolytic enzyme, and concentrations are based on the total weight of the mixture.

In an embodiment to the invention, content of chlorhexidine digluconate is 0.01% by weight to 0.12% by weight and the content of at least one proteolytic or hydrolytic enzyme is 0.01% by weight to 0.4% by weight.

An antiseptic and/or a disinfectant may be advantageously a salt of chlorhexidine, also a group of compounds derived from quaternary ammonium salts, including in particular benzalkonium chloride, cetylpyridinium chloride, benzoxonium chloride, dequalinium chloride or benzethonium chloride.

According to the invention, advantageous are also compounds of iodine and its derivatives, a group of phenolic compounds, hypochlorites, terpenes, peroxides, boric acid or acetic acid, sodium bicarbonate and a group of compounds, which includes compounds such as triclosan, tridecanamin, amylmetacresol, ambazone, gentian violet, benzydamine, flurbiprofen, hexetidine, dichlorobenzyl alcohol, amylmetacresol, hexylresorcinol, or mixtures thereof.

A salt of chlorhexidine, according to the invention, is chlorhexidine digluconate, although chlorhexidine hydrochloride or chlorhexidine acetate are also acceptable.

The inhibitor in the mixture may, advantageously to the invention, contains a mixture of antiseptic and/or disinfectant and two different enzymes, while more advantageous is a mixture of two hydrolytic enzymes.

According to the invention, an even more advantageous solution is, if the mixture of two hydrolytic enzymes is a mixture of protease, lipase or amylase, or of two proteases, lipases or amylases.

The most advantageous embodiment of the invention is a mixture of two proteases, which is a mixture of trypsin and bromelain, papain and bromelain, trypsin and chymotrypsin or chymotrypsin and bromelain.

An advantageous embodiment of the mixture of the invention further includes a solution of a mixture of two different hydrolytic or proteolytic enzymes, which additionally contains at least one further enzyme from the group consisting of oxidoreductase, transferase, hydrolase, lyase, isomerase, or ligase.

The mixture of the invention with an inhibitor of bacterial growth can, in addition to at least one hydrolytic or proteolytic enzyme, advantageously comprise a substance on a natural basis extracted from plants with anti-inflammatory, antibacterial or calming effects, whereas the substance on natural basis is advantageously an extract of cranberry, *Agrimonia eupatoria*, peppermint, *Matricaria chamomilla*, clove, fennel, *Salvia officinalis, Potentilla erecta*, or mixtures thereof.

The solution of the invention further comprises an agent for administration of the mixture of the invention to the mucous membrane and soft tissues of a mammal, i.e. a human or an animal.

Advantageous is the oral mucosa, genital mucosa or rectal mucosa, out of these the oral cavity is more advantageous.

Specifically, the agent is a toothpaste, tooth gel, mouthwash, lozenge, chewing gum, gargle, mouthwash, solution or paste for the gums, oral suspension, drops, spray, glaze, oral gel, sublingual, buccal, or chewable tablet, oral capsule, emulsion, cream, mucoadhesive film or disk.

The agent contains, together with the mixture, one or more commonly known and in the art used ingredients, such as water, humectants, fillers, whiteners, aromas, preservatives, thickeners, pH regulators, at least one enzyme stabilizer, sweetener, anticaries substance, abrasive medium, viscosity controller, or mucoadhesive polymers.

Advantageously, the inhibitor of bacterial growth in the mixture used in the agent according to the invention, contains a mixture containing 0.035% by weight chlorhexidine digluconate, 0.2% trypsin, 0.4% bromelain, based on the total weight of this agent.

The agent is, advantageously to the invention, a polyurethane foam comprising the mixture, and the foam is formed into a massage head for massaging the inside with the advantage of the dental cavity.

Another advantageous embodiment of the invention is the agent in the form of a polyurethane foam carrier with shape memory for teeth bite to adapt the shape of the carrier to the shape of the teeth, the subsequent removal of the carrier from the teeth, the application of the mixture into the cavity resulting from the effect of pressing into the carrier, and subsequent refitting of the carrier with the mixture onto the teeth.

The inventor verified the use of at least one proteolytic or hydrolytic enzyme in a bacterial growth inhibitor for a mucosa and the soft tissue of a mammal comprising the oral mucosa, genital mucosa or rectal mucosa. At least one mentioned enzyme can be used to reduce the content of an antiseptic and/or a disinfectant, which is advantageously a salt of chlorhexidine, in the inhibitor of bacterial growth in the mixture while maintaining the antimicrobial, antivirotic or antimycotic activity.

According to the invention, the mixture can be used advantageously for oral mucosa to inhibit the growth of bacteria involved in plaque formation, and subsequent formation of caries and parodontosis or to reduce discoloration of tooth enamel or tongue.

EXAMPLES

Example 1

Example 1 tested the hypothesis that an aqueous solution of chlorhexidine digluconate with variable concentration, with proteolytic enzymes with a constant concentration (fixed concentration) will form the same zone of inhibition of a mixed bacterial culture growth isolated from the saliva as a chlorhexidine solution on its own about twice the concentration. In view of the fact that cosmetic products, designed for hygiene of mucous membranes and the soft tissue of a mammal, i.e. a human or an animal, frequently use chlorhexidine in a concentration of 0.06% by weight and 0.12% by weight, these two concentrations were considered to be the reference mixtures (Sample 1, Sample 3). Mixtures which contained besides chlorhexidine digluconate also proteolytic enzymes were considered to be the tested mixtures (Sample 2, Sample 4).

The inhibitory potentials of chlorhexidine digluconate on its own (Biomedica s.r.o, Czech Republic) and the mixture of chlorhexidine digluconate and proteolytic enzymes of trypsin (2500 IU/mg, Biomedica s.r.o, Czech Republic) and bromelain (2000 GDU/g, Biomedica s.r.o, Czech Republic) were tested by a disk diffusion test.

Stock solutions were prepared of each substance; 1% by weight solution of chlorhexidine digluconate in $H_2O$; 1% by weight solution of trypsin in phosphate buffered saline (PBS); 1% by weight solution of bromelain in PBS. Mixtures (Table 1) of 1 ml were prepared from these stock solutions. Diagnostic discs (I-TEST PLUS s.r.o., Czech Republic) were immersed in the mixture for 3 minutes. Mixed bacterial culture isolated from saliva was aseptically triturated on the Petri dish with Brain Heart Infusion Agar (Oxoid; Thermo Fisher Scientific, UK) and individual diagnostic disks impregnated with the mixture were placed there. After incubation, which lasted 48 hours in 5% $CO_2$ atmosphere at 37° C., zones of inhibition were deducted using a ruler.

Figure 4:
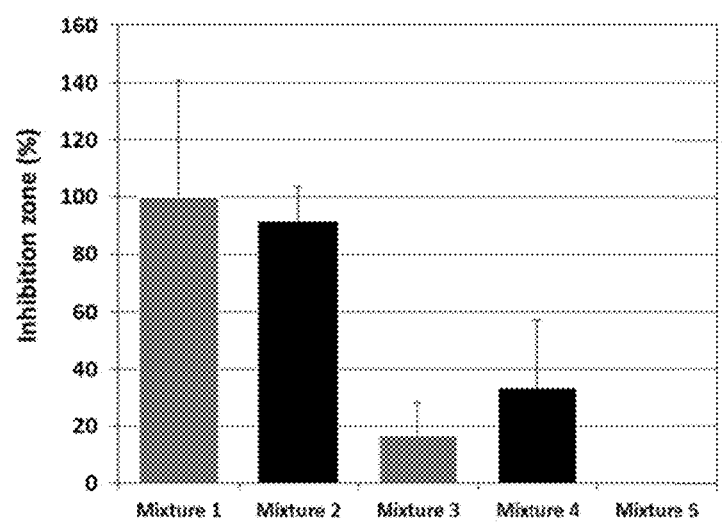

The results are shown in FIG. 4. During the experiment one concentration of trypsin (0.2% by weight) and bromelain (0.4% by weight) was tested.

TABLE 1

Tested mixtures of chlorhexidine digluconate and proteolytic enzymes.

| | % (wt.) |
|---|---|
| Mixture 1 | |
| Chlorhexidine digluconate | 0.12 |
| Trypsin | 0 |
| Bromelain | 0 |
| $H_2O$ | 99.88 |
| Mixture 2 | |
| Chlorhexidine digluconate | 0.06 |
| Trypsin | 0.2 |
| Bromelain | 0.4 |
| $H_2O$ | 99.34 |
| Mixture 3 | |
| Chlorhexidine digluconate | 0.06 |
| Trypsin | 0 |
| Bromelain | 0 |
| $H_2O$ | 99.94 |
| Mixture 4 | |
| Chlorhexidine digluconate | 0.03 |
| Trypsin | 0.2 |
| Bromelain | 0.4 |
| $H_2O$ | 99.37 |
| Mixture 5 | |
| Chlorhexidine digluconate | 0 |
| Trypsin | 0 |
| Bromelain | 0 |
| $H_2O$ | 100 |

The mixture of 0.06% by weight of chlorhexidine digluconate and proteolytic enzymes of trypsin and bromelain at a concentration of 0.2% by weight, or rather 0.4% by weight is able to inhibit the growth of the mixed culture isolated from the saliva equally well as the solution of chlorhexidine digluconate alone at a concentration of 0.12% by weight. The use of the given concentration of proteolytic enzymes in the mixture of chlorhexidine digluconate can reduce the concentration of chlorhexidine active substance 2× with the same bacteriostatic effect.

The mixture of 0.03% by weight of chlorhexidine digluconate and the proteolytic enzymes of trypsin and bromelain at a concentration of 0.2% by weight, or rather 0.4% (wt.) is able to inhibit the growth of the mixed culture isolated from the saliva roughly as well as the solution of chlorhexidine digluconate at a concentration of 0.06% by weight. Using proteolytic enzymes in a mixture with the active ingredient of chlorhexidine digluconate can reduce the concentration of chlorhexidine active substance 2× with the same bacteriostatic effect.

Example 2

Example 2 verified the minimum concentration of chlorhexidine digluconate (variable concentration) in combination with proteolytic enzymes with a constant concentration (fixed concentration) in aqueous solution which still has inhibitory effect on collection strains. Chlorhexidine digluconate in a concentration of 1% by weight (Sample 1) was taken as a reference. Mixtures which contained besides chlorhexidine digluconate also proteolytic enzymes were considered to be the tested mixtures (Sample 2 to Sample 5).

The inhibitory potentials of chlorhexidine digluconate on its own (Biomedica s.r.o, Czech Republic) and a mixture of chlorhexidine digluconate and proteolytic enzymes of trypsin ((2500 IU/mg, Biomedica s.r.o, Czech Republic) and bromelain (2000 GDU/g, Biomedica s.r.o, Czech Republic) were tested by a disk diffusion test.

Stock solutions were prepared of each substance; 1% by weight solution of chlorhexidine digluconate in $H_2O$; 1% by weight solution of trypsin in phosphate buffered saline (PBS); 1% by weight solution of bromelain in PBS. Mixtures (Table 2) of 1 ml were prepared from these stock solutions. Diagnostic discs (I-TEST PLUS s.r.o., Czech Republic) were immersed in the mixture for 3 minutes.

Suspensions of *Streptococcus mutans* (strain 6699, SZU, CZ), *Streptococcus salivarius* (strain 6713, SZU, CZ) or *Streptococcus sanguinis* (strain 6714, SZU, CZ) was aseptically triturated on the Petri dish with Brain Heart Infusion Agar (Oxoid; Thermo Fisher Scientific, UK) and individual diagnostic disks impregnated with the mixture were placed there. After incubation, which lasted 48 hours in 5% $CO_2$ atmosphere at 37° C., zones of inhibition were deducted using a ruler.

Figure 5:
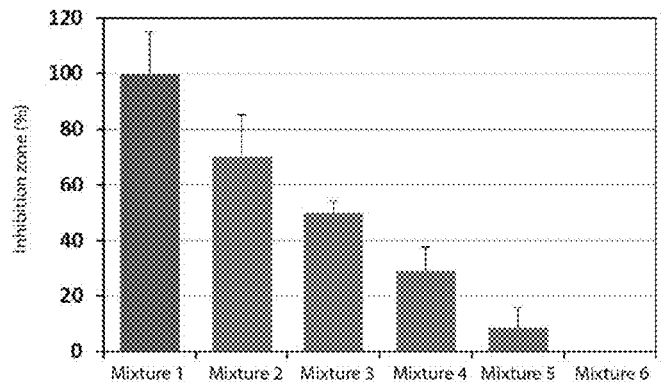
FIG. 5—Shows the effect of proteolytic enzymes on the amount of chlorhexidine digluconate required to inhibit the growth of collection strain *Streptococcus mutans*.
Figure 6:
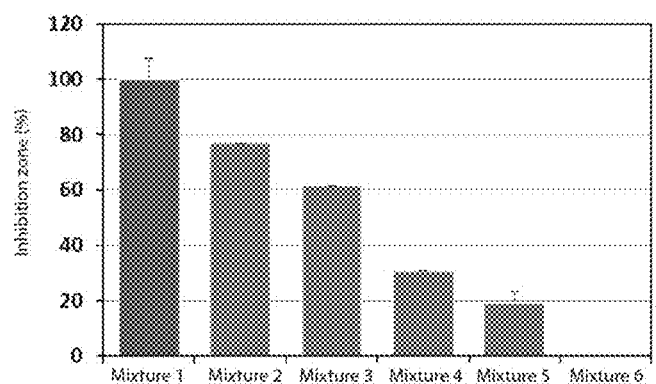
FIG. 6—Shows the effect of proteolytic enzymes on the amount of chlorhexidine digluconate required to inhibit the growth of collection strain *Streptococcus salivarius*.
Figure 7:
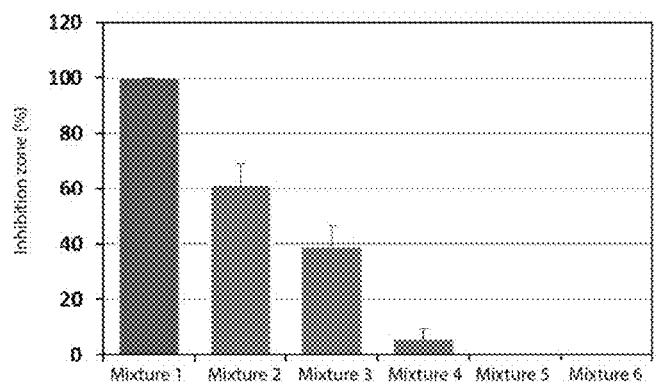
FIG. 7—Shows the effect of proteolytic enzymes on the amount of chlorhexidine digluconate required to inhibit the growth of collection strain *Streptococcus sanguinis*.

The results are summarized in FIGS. 5-7.

TABLE 2

Tested mixtures of chlorhexidine digluconate and proteolytic enzymes

| | % (wt.) |
|---|---|
| Mixture 1 | |
| Chlorhexidine digluconate | 1.0 |
| Trypsin | 0 |
| Bromelain | 0 |
| $H_2O$ | 99 |

TABLE 2-continued

Tested mixtures of chlorhexidine digluconate and proteolytic enzymes

| | % (wt.) |
|---|---|
| Mixture 2 | |
| Chlorhexidine digluconate | 0.12 |
| Trypsin | 0.2 |
| Bromelain | 0.4 |
| $H_2O$ | 99.28 |
| Mixture 3 | |
| Chlorhexidine digluconate | 0.06 |
| Trypsin | 0.2 |
| Bromelain | 0.4 |
| $H_2O$ | 99.34 |
| Mixture 4 | |
| Chlorhexidine digluconate | 0.03 |
| Trypsin | 0.2 |
| Bromelain | 0.4 |
| $H_2O$ | 99.37 |
| Mixture 5 | |
| Chlorhexidine digluconate | 0.01 |
| Trypsin | 0.2 |
| Bromelain | 0.4 |
| $H_2O$ | 99.39 |
| Mixture 6 | |
| Chlorhexidine digluconate | 0 |
| Trypsin | 0 |
| Bromelain | 0 |
| $H_2O$ | 100 |

The results show that the mixture of chlorhexidine digluconate in a concentration of 0.12% by weight used in the mixture with proteolytic enzymes retains about 70% inhibition effectiveness compared with the solution of chlorhexidine at a concentration of 1% by weight alone. In the case of collection strains of *Streptococcus mutans* and *Streptococcus salivarius*, growth inhibition was observed even at a concentration of 0.01% by weight of chlorhexidine digluconate in combination with the proteolytic enzymes.

Example 3

An Agent Containing a Volume of the Mixture of the Invention

The agent to the invention comprising the mixture is in the form of a toothpaste, a mucoadhesive gel with hydrophilic or hydrophobic properties with a possibility of administration to the oral cavity or the vaginal mucosa or the skin of a mammal, i.e. a human or an animal in the form of capsules or other lozenges, as a solution, or in another form such as a gel, which can be applied to the oral cavity, on other mucous membranes or on non-living materials.

An advantageous embodiment comprises 0.03-1% by weight of chlorhexidine digluconate and proteolytic enzymes mixture of trypsin and bromelain in concentrations of 0.01-2% by weight. This mixture may be enriched by other enzymes from the group of hydrolytic enzymes, directly proteolytic enzymes (e.g. chymotrypsin, papain, etc.). Or by other enzymes from the class of hydrolytic enzymes (e.g. lipase, amylase and others.).

Example 3a

An Agent Containing the Volume of the Mixture of the Invention Toothpaste

| Ingredient | % (by weight) |
|---|---|
| Glycerin anhydrous | 13 |
| Kelcogel CG LA | 0.1 |
| Water | 9.175 |
| Sorbit 70% | 49.72 |
| Sodium sacharinate | 0.05 |
| Sodium fluorid | 0.12 |
| Sodium benzoate | 0.6 |
| Chlorhexidine digluconate (20% wt.) | 0.175 |
| Magnesium sulphate | 0.05 |
| Hydrated silica | 20.8 |
| Trypsin | 0.2 |
| Bromelain | 0.4 |
| Menthol | 0.04 |
| Mint | 0.55 |
| Anethol | 0.02 |
| TEGO betain ZF | 5 |

Example 3b I

An Agent Containing the Volume of the Mixture of the Invention Mucoadhesive Gel

| Ingredient | % (by weight) |
|---|---|
| $H_2O$ | 91.24 |
| Glycerin | 3.5 |
| Hydroxyethylcelulose | 3.0 |
| Hydroxypropylmethylcelulose | 2.0 |
| Trypsin | 0.2 |
| Chlorhexidine digluconate | 0.06 |

Example 3b II

An Agent Containing the Volume of the Mixture of the Invention Mucoadhesive Gel

| Ingredient | % (by weight) |
|---|---|
| $H_2O$ | 91.19 |
| Glycerin | 3.5 |
| Hydroxyethylcelulose | 3.0 |
| Hydroxypropylmethylcelulose | 2.0 |
| Trypsin | 0.2 |
| Chlorhexidine digluconate | 0.06 |
| Cetylpyridinium chloride | 0.05 |

Example 3b III

An Agent Containing the Volume of the Mixture of the Invention Mucoadhesive Gel

| Ingredient | % (by weight) |
|---|---|
| $H_2O$ | 90.465 |
| Glycerin | 3.5 |

-continued

| Ingredient | % (by weight) |
|---|---|
| Hydroxyethylcelulose | 3.0 |
| Hydroxypropylmethylcelulose | 2.0 |
| Sodium benzoate | 0.8 |
| Trypsin | 0.2 |
| Chlorhexidine digluconate | 0.035 |

Example 4

Example 4 verified the inhibitory ability of the agent of the invention, a toothpaste according to Example 3a (Sample 1) compared with widely available industrially produced agents (products) (Samples 2-5) containing only chlorhexidine digluconate in different concentrations, and for comparison a toothpaste according to Example 3a, but without the addition of chlorhexidine and proteolytic enzymes (Sample 6) as shown in Table 3.

Figure 1:
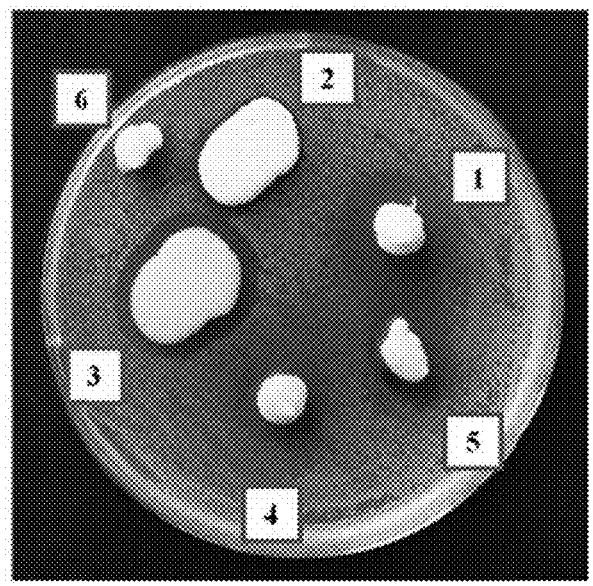
FIG. 1—Shows the different sizes of zones of inhibition 1-6 of the mixture according to the invention compared to the art FIG. 2—Shows the size of zones of inhibition 1-3 depending on the concentration of chlorhexidine digluconate according to art, and with mixture according to the invention FIG. 3—Shows the size of zones of inhibition 1-3 of the mixture according to the invention compared to the art FIG. 4—Shows the effect of proteolytic enzymes on the amount of chlorhexidine digluconate required to inhibit the growth of a mixed bacterial culture.

Suspensions of *Escherichia coli* (typical example of gram-negative facultative anaerobic microorganism), was aseptically triturated on the Petri dish with Lauria Broth agar (Oxoid; Thermo Fisher Scientific, UK). Immediately 0.4 ml of each sample was placed there. After incubation, which lasted 24 hours at 35° C., zones of inhibition were detected (FIG. 1).

TABLE 3

List of examined application samples

| Sample | | Chlorhexidine digluconate concentration [% by weight] |
|---|---|---|
| 1 | Mixture of an advantageous embodiment of the invention - Example 3a | 0.035 |
| 2 | Commercially available toothpaste 1 | 0.06 |
| 3 | Commercially available toothpaste 2 | 0.12 |
| 4 | Commercially available toothpaste 3 | 0.12 |
| 5 | Commercially available toothpaste 4 | 0.2 |
| 6 | Mixture of an advantageous embodiment of the invention - Example 3a: without addition of chlorhexidine digluconate and proteolytic enzymes | 0 |

FIG. 1 shows that the mixture of an advantageous embodiment of the invention—Example 3a, which is a toothpaste (Sample 1) forms a wide zone of inhibition. On the contrary, this zone cannot be observed with the mixture of an advantageous embodiment of the invention—Example 3a—a toothpaste without the addition of chlorhexidine and proteolytic enzymes (Sample 6), which is fully in line with the assumption.

Furthermore, FIG. 1 shows that sample 1 forms a comparable or wider zone of inhibition than a widely available toothpaste 4 (Sample 5) having a concentration of chlorhexidine digluconate 0.2% by weight. Diffluence was observed in Samples 2 and 3, which can be attributed to the specific composition of the products, while exposing the samples to constant temperature of 35° C.

Therefore, it can be concluded that the proposed mixture of the advantageous embodiment—a toothpaste (Sample 1) with chlorhexidine digluconate at a concentration of 0.035% by weight and proteolytic enzymes trypsin at a concentration of 0.2% by weight and bromelain at a concentration of 0.4% by weight inhibits in vitro microbial growth at least as well as a widely available toothpaste containing chlorhexidine digluconate at a concentration of 0.2% by weight. During concomitant administration of proteolytic enzymes and chlorhexidine it is, therefore, possible to reduce the concentration of chlorhexidine in the mixtures 5-6 times while maintaining the same inhibitory activity of the mixture.

Example 5

Example 5 verified inhibitory ability of the agent comprising chlorhexidine and one proteolytic enzyme (trypsin—2500 IU/mg) in the form of gel (embodiment example 3b I) in comparison with the agents—gels (products) containing only chlorhexidine digluconate in various concentrations (Table 4a).

Figure 2:
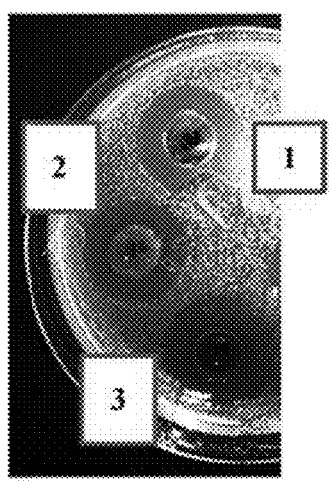

Suspensions of *Escherichia coli* (typical example of gram-negative facultative anaerobic microorganism), was aseptically triturated on the Petri dish with Lauria Broth agar (Oxoid; Thermo Fisher Scientific, UK). Immediately 0.4 ml of each sample was placed there. After incubation, which lasted 24 hours at 35° C., zones of inhibition were detected (FIG. 2).

TABLE 4a

List of examined application samples

| Sample | | Chlorhexidine digluconate concentration [% (wt.)] |
|---|---|---|
| 1 | Mixture of an advantageous embodiment of the invention - Example 3b I | 0.06 |
| 2 | Commercially available gel 1 | 0.15 |
| 3 | Commercially available gel 2 | 0.5 |

FIG. 2 shows that the mixture of the advantageous embodiment of the invention—Example 3b I: a mucoadhesive gel (Sample 1) forms the wide zone of inhibition wider than that which is observable with widely available gel 1 containing chlorhexidine digluconate at a concentration of 0.15% by weight, and smaller than commonly available gel 2 containing chlorhexidine digluconate at a concentration of 0.5% by weight.

Therefore, it can be concluded that the proposed mixture of an advantageous embodiment—a mucoadhesive gel (Sample 1) with chlorhexidine digluconate at a concentration of 0.06% by weight and a proteolytic enzyme trypsin at a concentration of 0.2% by weight inhibits in vitro microbial growth clearly better than a comparable product containing chlorhexidine at a concentration of 0.15% by weight, and worse than a comparable product with chlorhexidine at a concentration of 0.5% by weight. During concomitant administration of one proteolytic enzyme and chlorhexidine digluconate it is, therefore, possible to reduce the concentration of chlorhexidine digluconate in the mixture 2.5-3 times while maintaining the same inhibitory activity of the mixture.

Example 6

Example 6 tested inhibitory ability of the agent comprising chlorhexidine and one proteolytic enzyme (trypsin—2500 IU/mg) in the form of gel (embodiment example 3b III) in comparison with the agents—gels containing only chlorhexidine digluconate in different concentrations, or Example 3b III—an embodiment of the invention, but without the addition of chlorhexidine and proteolytic enzymes (Table 4b).

Figure 3:
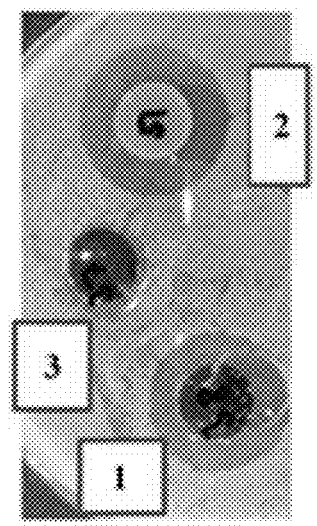

Suspensions of *Escherichia coli* (typical example of gram-negative facultative anaerobic microorganism), was aseptically triturated on the Petri dish with Lauria Broth agar (Oxoid; Thermo Fisher Scientific, UK). Immediately 0.4 ml of each sample was placed there. After incubation, which lasted 24 hours at 35° C., zones of inhibition were detected (FIG. 3).

TABLE 4b

List of examined application samples

| Sample | | Chlorhexidine digluconate concentration [% (wt.)] |
|---|---|---|
| 1 | Mixture of an advantageous embodiment of the invention - Example 3b III | 0.035 |
| 2 | Commercially available gel 1 | 0.15 |
| 3 | Mixture of an advantageous embodiment of the invention - Example 3b III: without addition of chlorhexidine digluconate and proteolytic enzymes | 0 |

FIG. 3 shows that the mixture of the advantageous embodiment of the invention—Example 3b III: a mucoadhesive gel (Sample 1) forms a similarly wide zone of inhibition which is observable with widely available gel 1 containing chlorhexidine digluconate at a concentration of 0.15% by weight.

On the contrary, this zone cannot be observed with the mixture of an advantageous embodiment of the invention—Example 3b III—a mucoadhesive gel without the addition of chlorhexidine and proteolytic enzymes (Sample 3), which is fully in line with the assumption.

Therefore, it can be concluded that the proposed mixture of an advantageous embodiment—a mucoadhesive gel (Sample 1) with chlorhexidine digluconate at a concentration of 0.035% by weight and a proteolytic enzyme trypsin at a concentration of 0.2% by weight inhibits in vitro microbial growth similar to a comparable product containing chlorhexidine at a concentration of 0.15% by weight. During concomitant administration of one proteolytic enzyme and chlorhexidine digluconate it is therefore possible to reduce the concentration of chlorhexidine digluconate in the mixture 2.5-3 times while maintaining the same inhibitory activity of the mixture.

Example 7

Example 7 tested the hypothesis that an aqueous solution of chlorhexidine digluconate with proteolytic enzymes will form the same zone of inhibition of a bacterial culture growth as a chlorhexidine solution on its own with about twice the concentration. A chlorhexidine solution at a concentration of 0.06% by weight was considered a reference mixture (Sample 1). A mixture which contained besides chlorhexidine digluconate also proteolytic enzymes was considered to be the tested mixture (Sample 2).

The inhibitory potentials of chlorhexidine digluconate on its own (Biomedica s.r.o, Czech Republic) and the mixture of chlorhexidine digluconate and proteolytic enzymes of chymotrypsin (1000 IU/mg, Biomedica s.r.o, Czech republic) a papain (80000 IU/g, Biomedica s.r.o, Czech republic) were tested by a disk diffusion test.

Stock solutions were prepared of each substance; 1% by weight solution of chlorhexidine digluconate in $H_2O$; 1% by weight solution of chymotrypsin in phosphate buffered saline (PBS); 1% by weight solution of papain in PBS. Mixtures (Table 5) of 1 ml were prepared from these stock solutions. Diagnostic discs (I-TEST PLUS s.r.o., Czech Republic) were immersed in the mixture for 3 minutes. Suspensions of *Escherichia coli* (typical example of gram-negative facultative anaerobic microorganism), was aseptically triturated on the Petri dish with Lauria Broth agar (Oxoid; Thermo Fisher Scientific, UK) and individual diagnostic disks impregnated with the mixture were placed there. After incubation, which lasted 24 hours at 35° C., zones of inhibition were detected.

Figure 8:
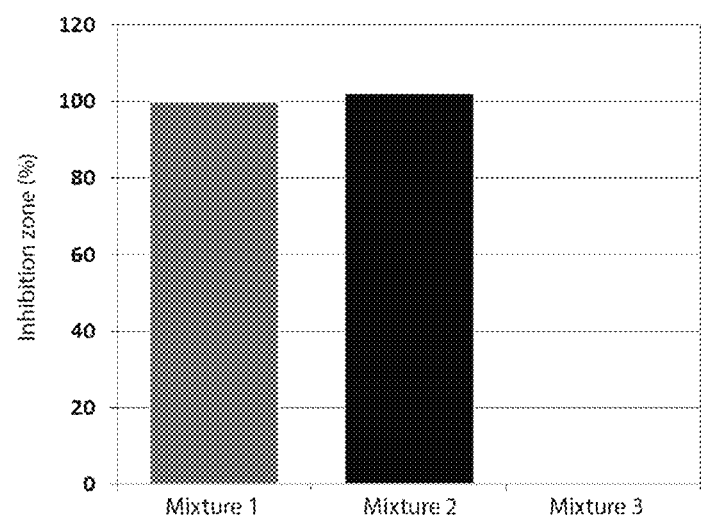
FIG. 8—Shows the effect of proteolytic enzymes on the amount of chlorhexidine digluconate required to inhibit the growth of a bacterial culture.

The results are shown in FIG. 8.

TABLE 5

Tested mixtures of chlorhexidine digluconate and proteolytic enzymes.

| | % (wt.) |
|---|---|
| Mixture 1 | |
| Chlorhexidine digluconate | 0.06 |
| Chymotrypsin | 0 |
| Papain | 0 |
| $H_2O$ | 99.94 |
| Mixture 2 | |
| Chlorhexidine digluconate | 0.03 |
| Chymotrypsin | 0.2 |
| Papain | 0.4 |
| $H_2O$ | 99.37 |
| Mixture 3 | |
| Chlorhexidine digluconate | 0 |
| Chymotrypsin | 0 |
| Papain | 0 |
| $H_2O$ | 100 |

The mixture of 0.03% by weight of chlorhexidine digluconate and the proteolytic enzymes of chymotrypsin and papain at a concentration of 0.2% by weight, or rather 0.4% by weight is able to inhibit the growth of a bacterial culture equally well as the solution of chlorhexidine digluconate alone at a concentration of 0.06% by weight. The use of the given concentration of proteolytic enzymes in the mixture of chlorhexidine digluconate can reduce the concentration of chlorhexidine active substance 2× with the same bacteriostatic effect.

Example 8

Nine volunteers were divided into 3 groups. Volunteers in Group 1 used for oral hygiene an agent containing the mixture according to Example 3a. Volunteers in Group 2 used for oral hygiene an agent containing chlorhexidine 0.12% by weight. Volunteers in Group 3 used for oral hygiene an agent containing chlorhexidine 0.06% by weight. Papilla Bleeding Index (PBI) was measured in all volunteers and their oral pathogens analysis carried out using PCR chromosomal DNA on day 0 and after 30 days of use of the agent. Characteristics of volunteers: without antibiotic treatment for at least 3 months, non-smokers, without hormonal contraception, age 35-50 years.

Results of PBI values are given in Table 6. The results of genetic analysis of oral pathogens are shown in Table 7.

TABLE 6

Results of PBI estimation

| Group | Active compounds | Volunteer | Day 0 | Day 30 | Improvement (%) |
|---|---|---|---|---|---|
| 1 | Chlorhexidine digluconate 0.035% trypsin 0.2% bromelain 0.4% | 1 | 2.8 | 1.6 | 43 |
| | | 2 | 2.5 | 2.3 | 8 |
| | | 3 | 2.1 | 1.6 | 25 |
| 2 | Chlorhexidine digluconate 0.12% | 4 | 3.1 | 2.7 | 12 |
| | | 5 | 2.6 | 2.3 | 9 |
| | | 6 | 2.4 | 2.3 | 4 |
| 3 | Chlorhexidine digluconate 0.06% | 7 | 3.0 | 3.0 | 3 |
| | | 8 | 2.3 | 2.4 | −8 |
| | | 9 | 2.3 | 2.4 | −4 |

TABLE 7

Results of oral pathogens analysis

| Group | Active compounds | Volunteer | Day | PG | TF | TD | PI | AA |
|---|---|---|---|---|---|---|---|---|
| 1 | Chlorhexidine digluconate 0.035% trypsin 0.2% bromelain 0.4% | 1 | 0 | + | + | + | + | 0 |
| | | | 30 | + | + | + | 0 | 0 |
| | | 2 | 0 | + | + | + | + | 0 |
| | | | 30 | + | + | + | + | 0 |
| | | 3 | 0 | + | + | 0 | 0 | 0 |
| | | | 30 | 0 | 0 | 0 | 0 | 0 |
| 2 | Chlorhexidine digluconate 0.12% | 4 | 0 | + | + | + | + | + |
| | | | 30 | + | + | + | + | + |
| | | 5 | 0 | + | + | 0 | 0 | 0 |
| | | | 30 | + | + | 0 | 0 | 0 |
| | | 6 | 0 | + | + | 0 | 0 | 0 |
| | | | 30 | 0 | + | 0 | 0 | 0 |
| 3 | Chlorhexidine digluconate 0.06% | 7 | 0 | + | 0 | + | 0 | + |
| | | | 30 | + | 0 | + | 0 | + |
| | | 8 | 0 | + | 0 | 0 | 0 | 0 |
| | | | 30 | 0 | 0 | 0 | 0 | 0 |
| | | 9 | 0 | + | + | + | 0 | 0 |
| | | | 30 | + | + | + | 0 | 0 |

The abbreviations used in Table 7:
Oral pathogens:
PG - *Porphyromonas gingivalis*;
TF - *Tannerella forsythia*;
TD - *Treponema denticola*;
PI - *Prevotella intermedia*;
AA - *Aggregatibacter actinomycetemcomitans*.
"+" - identified;
"0" - not identified.

At the end of a 30-day period during which volunteers used an agent containing the mixture according to Example 3a (chlorhexidine digluconate at a concentration of 0.06% by weight, trypsin 0.2% by weight, bromelain 0.4% by weight), all volunteers had their bleeding index (PBI) reduced by 8-43% compared to initial values. Bacteria load count of two volunteers changed for the better. The group of volunteers using during their oral hygiene procedure an agent with chlorhexidine at a concentration of 0.12% had their bleeding index (PBI) decreased by about 4-12% compared to initial values. Bacteria load count of two volunteers changed for the better. The group of volunteers using during their oral hygiene procedure an agent with chlorhexidine at a concentration of 0.06% did not have their bleeding index (PBI) reduced. Bacteria load count of one patient changed for the better.

INDUSTRIAL APPLICATION

It is evident that products containing proteolytic enzymes directly reduce the risk of adverse effects caused by the salts of chlorhexidine. Above all, because it is possible to use significantly smaller amounts of salts of chlorhexidine like the chlorhexidine digluconate whilst achieving the same inhibition of bacterial growth, and thus suppress the negative effects during the prevention or treatment of antimicrobial, antivirotic or antimycotic illnesses.

The invention claimed is:

1. An antiseptic or a disinfectant composition comprising chlorhexidine digluconate in an amount of 0.001% to 1% by weight and proteolytic or hydrolytic enzyme in an amount of 0.01% to 2% by weight based on the total weight of the composition and further comprising buffered saline and water.

2. The antiseptic or a disinfectant composition according to claim 1, wherein the amount of chlorhexidine digluconate is 0.01% to 0.12% by weight and the amount of proteolytic or hydrolytic enzyme is 0.01% to 0.4% by weight based on the total weight of the composition.

3. The antiseptic or a disinfectant composition according to claim 1, comprising two different enzymes.

4. The antiseptic or a disinfectant composition according to claim 3, wherein the two different enzymes are each a hydrolytic enzyme.

5. The antiseptic or a disinfectant composition according to claim 4, wherein the hydrolytic enzyme is selected from protease, lipase or amylase.

6. The antiseptic or a disinfectant composition according to claim 1, comprising two hydrolytic enzymes, wherein the two hydrolytic enzymes are both proteases, lipases or amylases.

7. The antiseptic or a disinfectant composition according to claim 6, wherein the protease is selected from the group consisting of trypsin, chymotrypsin, bromelain and papain.

8. The antiseptic or a disinfectant composition according to claim 7, wherein the amount of chlorhexidine digluconate is 0.001% to 1% by weight, the amount of trypsin or chymotrypsin is 0.01% to 0.2% by weight and the content of bromelain is 0.01% to 0.4% by weight based on the total weight of the composition.

9. The antiseptic or a disinfectant composition according to claim 8, wherein the amount of chlorhexidine digluconate is 0.035% by weight, the amount of trypsin or chymotrypsin is 0.2% by weight and the content of bromelain is 0.4% by weight based on the total weight of the composition.

10. The antiseptic or a disinfectant composition according to claim 1, further comprising a natural extract from a plant with anti-inflammatory, antibacterial or calming effect.

11. The antiseptic or a disinfectant composition according to claim 10, wherein the extract is selected from the group consisting of cranberry, Agrimonia *eupatoria*, peppermint, *Matricaria* chamomile, clove, fennel, *Salvia officinalis*, *Potentilla erecta*, and a mixtures thereof.

12. The antiseptic or a disinfectant composition according to claim 1, further comprising humectant, filler, whitener, aroma, preservative, thickener, pH regulator, enzyme stabilizer, sweetener, anticaries substance, abrasive substance, viscosity regulator, or mucoadhesive polymer.

13. A method of treating microbial, viral or mycotic illnesses or reducing discoloration of tooth enamel or tongue, the method comprising administering the composition according to claim 1 to a subject in need thereof.

14. The method of claim 13, wherein the microbial illness is related to plaque formation, and subsequent formation of caries and periodontitis.

15. The method of claim 13, wherein the composition is administered orally.

16. The method of claim 13, wherein the composition is in the form of toothpaste, tooth gel, mouthwash, lozenge, chewing gum, gargle, mouthwash, solution or paste for the gums, oral suspension, drops, spray, glaze, oral gel, sublingual, buccal, or chewable tablet, oral capsule, emulsion, cream, mucoadhesive film or disk.

17. A method of treating inanimate surface comprising the step of contacting the composition according to claim 1 with the inanimate surface.

\* \* \* \* \*